(12) United States Patent
Gerberding

(10) Patent No.: US 7,060,083 B2
(45) Date of Patent: Jun. 13, 2006

(54) FOLDABLE VASO-OCCLUSIVE MEMBER

(75) Inventor: Brent Gerberding, Alameda, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 480 days.

(21) Appl. No.: 10/152,441

(22) Filed: May 20, 2002

(65) Prior Publication Data
US 2003/0216757 A1 Nov. 20, 2003

(51) Int. Cl.
*A61M 29/00* (2006.01)

(52) U.S. Cl. ......................... 606/200; 606/191

(58) Field of Classification Search .............. 606/200, 606/191
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 4,994,069 A | 2/1991 | Ritchart et al. | |
| 5,122,136 A | 6/1992 | Guglielmi et al. | |
| 5,234,437 A | 8/1993 | Sepetka | |
| 5,250,071 A | 10/1993 | Palermo | |
| 5,261,916 A | 11/1993 | Engelson | |
| 5,290,552 A | 3/1994 | Sierra et al. | |
| 5,304,195 A | 4/1994 | Twyford, Jr. et al. | |
| 5,312,415 A | 5/1994 | Palermo | |
| 5,350,397 A | 9/1994 | Palermo et al. | |
| 5,354,295 A | 10/1994 | Guglielmi et al. | |
| 5,423,829 A | 6/1995 | Pham et al. | |
| 5,669,931 A | 9/1997 | Kupiecki et al. | |
| 5,690,666 A | 11/1997 | Berenstein et al. | |
| 5,826,587 A | 10/1998 | Berenstein et al. | |
| 6,041,785 A | 3/2000 | Webb | |
| 6,168,788 B1 | 1/2001 | Wortham | |
| 6,245,090 B1 | 6/2001 | Gilson et al. | |
| 6,280,457 B1 | 8/2001 | Wallace et al. | |
| 6,322,576 B1 | 11/2001 | Wallace et al. | |
| 6,585,753 B1 * | 7/2003 | Eder et al. ................. | 623/1.15 |
| 2001/0025155 A1 | 9/2001 | Inbae | |
| 2002/0016613 A1 | 2/2002 | Daniel et al. | |
| 2002/0077693 A1 * | 6/2002 | Barclay et al. ............. | 623/1.13 |
| 2002/0193819 A1 * | 12/2002 | Porter ........................ | 606/191 |

\* cited by examiner

*Primary Examiner*—Gary Jackson
(74) *Attorney, Agent, or Firm*—Bingham McCutchen LLP

(57) ABSTRACT

Vaso-occlusive devices for occlusion of a body cavity are provided. The vaso-occlusive devices include an elongate vaso-occlusive member having one or more fold lines. Methods of using the vaso-occlusive devices are also described.

64 Claims, 11 Drawing Sheets

FOLDABLE VASO-OCCLUSIVE MEMBER

BACKGROUND OF THE INVENTION

1. Field of the Invention

The field of the invention pertains to implantable devices, and, more particularly, vaso-occlusive devices for the occlusion of body lumens and cavities.

2. Background of the Invention

In many clinical situations, blood vessels are occluded for a variety of purposes, such as to control bleeding, to prevent blood supply to tumors, and to block blood flow within an aneurysm.

Embolization of blood vessels is particularly useful in treating aneurysms. Aneurysms are abnormal blood filled dilations of a blood vessel wall, which may rupture causing significant bleeding. For the cases of intracranial aneurysms, the significant bleeding may lead to damage to surrounding brain tissue or death. Intracranial aneurysms may be difficult to treat when they are formed in remote cerebral blood vessels, which are very difficult to access. If left untreated, hemodynamic forces of normal pulsatile blood flow can rupture fragile tissue in the area of the aneurysm causing a stroke.

Vaso-occlusive devices have been used in the treatment of aneurysms. Vaso-occlusive devices are surgical implants placed within blood vessels or vascular cavities, typically by the use of a catheter, to form a thrombus and occlude the site. For instance, treatment of a stroke or other such vascular accident may include the placement of a vaso-occlusive device proximal of the site to block the flow of blood to the site and alleviate the leakage. An aneurysm may similarly be treated by introduction of a vaso-occlusive device through the neck of the aneurysm. The thrombogenic properties of the vaso-occlusive device cause a mass to form in the aneurysm and alleviate the potential for growth of the aneurysm and its subsequent rupture. Other diseases, such as tumors, may often be treated by occluding the blood flow to the tumor.

There are a variety of vaso-occlusive devices suitable for forming thrombi. One such device is found in U.S. Pat. No. 4,994,069, to Ritchart et al., the entirety of which is incorporated by reference. That patent describes a vaso-occlusive coil that assumes a linear helical configuration when stretched and a folded convoluted configuration when relaxed. The stretched configuration is used in placement of the coil at the desired site and the convoluted configuration occurs when the coil is ejected from the catheter and the coil relaxes. Ritchart et al. describes a variety of shapes, including "flower" shapes and double vortices. A random shape is described as well.

U.S. Pat. No. 6,280,457B1 to Wallace et al., describes an occlusive device comprising an inner core wire covered with a polymer. The polymeric material includes protein based polymers, absorbable polymers, non-protein based polymers, and combinations thereof. The polymer helps contribute to the formation of emboli for occlusion of a body cavity.

Vaso-occlusive coils having complex, three-dimensional structures in a relaxed configuration are described in U.S. Pat. No. 6,322,576B1 to Wallace et al. The coils may be deployed in the approximate shape of a sphere, an ovoid, a clover, a box-like structure or other distorted spherical shape. The patent also describes methods of winding an anatomically shaped vaso-occlusive device into appropriately shaped forms and annealing them to form various devices.

Vaso-occlusive coils having little or no inherent secondary shape have also been described. For instance, co-owned U.S. Pat. Nos. 5,690,666 and 5,826,587 by Berenstein et al., describe coils having little or no shape after introduction into the vascular space.

There are a variety of ways of discharging shaped coils and linear coils into a body cavity. In addition to those patents that apparently describe only the physical pushing of a coil out into the body cavity (e.g., Ritchart et al.), there are a number of other ways to release the coil at a specifically chosen time and site. U.S. Pat. No. 5,354,295 and its parent, 5,122,136, both to Guglielmi et al., describe an electrolytically detachable embolic device.

A variety of mechanically detachable devices are also known. Various examples of these devices are described in U.S. Pat. No. 5,234,437, to Sepetka, U.S. Pat. No. 5,250,071 to Palermo, U.S. Pat. No. 5,261,916, to Engelson, U.S. Pat. No. 5,304,195, to Twyford et al., U.S. Pat. No. 5,312,415, to Palermo, and U.S. Pat. No. 5,350,397, to Palermo et al.

Vaso-occlusive devices may be composed of biodegradable materials, such as polyglygolic acid polymer, and/or non-biodegradable materials, such as metal. Biodegradable vaso-occlusive devices may not have the required resilient or stiffness to form a desired three dimensional relaxed configuration. As such, it is desirable to have an improved vaso-occlusive device that does not require a convoluted or complex three dimensional relaxed configuration. Furthermore, it is also desirable to have an improved vaso-occlusive device that conforms better with the shape of a body cavity and has a more efficient space-filling capacity.

SUMMARY OF THE INVENTION

The present inventions are directed to a vaso-occlusive device that can be deployed within the vasculature of a patient to occlude the flow of blood therein. Preferably, the inventive vaso-occlusive device is deployed to provide emboli in aneurysms located within the vasculatures of humans, but may also be used at any site in a human or animal that requires occlusion. In providing occlusion, the vaso-occlusive device includes an elongate vaso-occlusive member that can be deployed into one of any variety of shapes to conform to the occlusion site. The inventive vaso-occlusive device can be carried to the target site using a catheter and released therefrom using any one of a variety of detachable means, such as an electrolytic joint.

The vaso-occlusive device includes one or more fold lines along which the vaso-occlusive may fold when it is subjected to an external force or pressure. The fold line may be formed, for example, by a key-way disposed on the vaso-occlusive member. The key-way(s) can be formed on the member using a variety of means, including laser-etching, mechanical removal of a portion of the vaso-occlusive member, and injection molding. The key-way(s) can also be formed during extrusion of the vaso-occlusive member in the manufacturing process.

The key-way(s) may be variously formed to provide the advantageous fold line(s). The key-way(s) can have any suitable cross-section, e.g., rectangular or triangular. The widths and depths of the key-way(s) can vary to advantageously promote specific fold lines along the length of the vaso-occlusive member. The number and pattern of the key-way(s) can also vary to promote specific fold lines.

For example, the key-way(s) can be disposed continuously along portion(s) of the vaso-occlusive device. In which case, the folding of the vaso-occlusive member may occur anywhere along the vaso-occlusive device, and the direction of fold line would coincide with the pitch of the key-way at the corresponding location at which the folding occurs. The vaso-occlusive device can have a single pitched key-way or multiple pitched key-ways that extend along the member. In the latter case, the key-ways can be axially spaced from each other. Alternatively, the multiple key-ways can be disposed along the member in an intersecting fashion.

As another example, the key-way(s) is not disposed continuously along portion(s) of the vaso-occlusive device, but is disposed discretely along the device. The key-way(s) can be partially disposed around the circumference of the member to provide directionally in the folding, or can be disposed completely around the circumference of the member so that there is no directionality in the folding. The key-way(s) can also be pitched. Furthermore, the key-way(s) can be formed in groups along portion(s) of the vaso-occlusive device to further weaken the vaso-occlusive device at the corresponding portion(s).

Although the present inventions should not necessarily be so limited, the folding patterns of the inventive vaso-occlusive device allow it to more efficiently and easily fill the body cavity space even if the vaso-occlusive device is linear and does not have a secondary or tertiary shape, although the space filling capacities of vaso-occlusive devices with secondary and tertiary shapes can improved with the present inventions. In this regard, the present inventions lend themselves well to vaso-occlusive devices composed of biodegradable material, but also provide benefits to non-biodegradable vaso-occlusive devices also.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
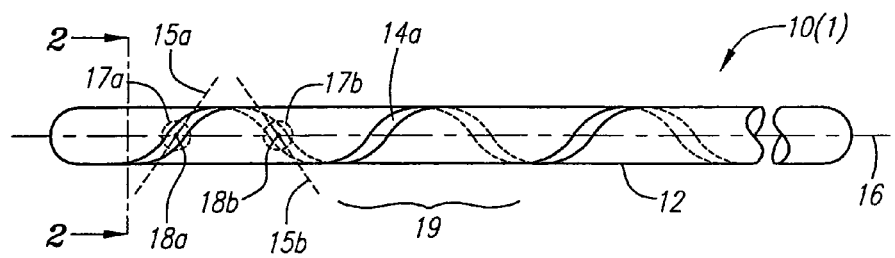
FIG. 1 is a side view of one variation of a foldable vaso-occlusive device constructed in accordance with a first preferred embodiment of the present inventions, particularly showing a key-way disposed continuously along the vaso-occlusive member.

Referring to FIGS. 1–6, various preferred embodiments of vaso-occlusive devices 10 will be described. Each of the devices 10 includes an elongate vaso-occlusive member 12, and one or more key-ways 14 formed within the vaso-occlusive member 12. As will be described in further detail below, the key-way(s) 14 weaken the axial and flexural strength of the member 12 and causes the vaso-occlusive member 12 to be more susceptible to being folded along a fold line in a certain direction when the device 10 is subjected to an external force, i.e., when the device 10 comes in contact with an object, such as the wall of a body cavity.

The vaso-occlusive member 12 preferably has a circular cross-sectional shape. Alternatively, the vaso-occlusive member 12 may have rectangular, a triangular, or other geometric cross-sections. The vaso-occlusive member 12 may even have an irregular shaped cross-section.

The vaso-occlusive member 12 is preferably made of biodegradable materials. Biodegradable or absorbable materials suitable for use in the compositions of the vaso-occlusive member 12 include, but are not limited to, polymers and proteins. Suitable polymers include, for example, polyglycolic acid (PGA), poly-glycolic/poly-L-lactic acid co-polymers, polycaprolactone, polyhydroxybutyrate/hydroxyvalerate copolymers, poly-L-lactide, polydioxanone, polycarbonates, and polyanhydrides. Non-limiting examples of bioabsorbable proteins include collagen, elastin, fibrinogen, fibronectin, vitronectin, laminin and gelatin. Many of these materials are commercially available. Fibrin-containing compositions are commercially available, for example from Baxter. Collagen containing compositions are commercially available, for example, from Cohesion Technologies, Inc., Palo Alto, Calif. Fibrinogen-containing compositions are described, for example, in U.S. Pat. Nos. 6,168,788 and 5,290,552, the entirety of which is hereby incorporated by reference. As will be readily apparent, absorbable materials can be used alone or in any combination with each other. The absorbable material may be in the form of a mono-filament or, alternatively, a multi-filament strands.

Furthermore, the absorbable materials may be used in combination with additional components. For example, lubricious materials (e.g., hydrophilic) materials may be used to coat the member to help facilitate delivery. One or more bioactive materials may also be included in the composition of the vaso-occlusive member 12. The term "bioactive" refers to any agent that exhibits effects in vivo, for example a thrombotic agent, a therapeutic agent or the like. Non-limiting examples of bioactive materials include cytokines; extracellular matrix molecules (e.g., collagen); trace metals (e.g., copper); and other molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1) or the like). Non-limiting examples of cytokines which may be used alone or in combination in the practice of the present invention include, basic fibroblast growth factor (bFGF), platelet derived growth factor (pDGF), vascular endothelial growth factor (VEGF), transforming growth factor beta (TGF-$\beta$) and the like. Cytokines, extracellular matrix molecules, and thrombus stabilizing molecules are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additionally, bioactive polypeptides can be synthesized recombinantly as the sequence of many of these molecules are also available, for example, from the GenBank database. Thus, it is intended that the invention include use of DNA or RNA encoding any of the bioactive molecules. Furthermore, it is intended that molecules having similar biological activity as wild-type or purified cytokines, extracellular matrix molecules and thrombus-stabilizing proteins (e.g., recombinantly produced or mutants thereof) and nucleic acid encoding these molecules may also be used. The amount and concentration of the bioactive materials that may be included in the composition of the vaso-occlusive member 12 may vary, depending on the specific application, and can be readily determined by one skilled in the art. It will be understood that any combination of materials, concentration or dosage can be used, so long as it is not harmful to the subject.

For the compositions of the vaso-occlusive member 12, it may also be desirable to include one or more radiopaque materials for use in visualizing the vaso-occlusive members 12 in situ. Thus, the vaso-occlusive members 12 may be coated or mixed with radiopaque materials such as metals (e.g. tantalum, gold, tungsten or platinum), barium sulfate, bismuth oxide, bismuth subcarbonate, and the like.

Alternatively, the vaso-occlusive member 12 may be made of non-biodegradable materials, such as metals or alloys, for examples, that are in general more elastic than the biodegradable materials described previously. Suitable metals and alloys for the wire making up the coil include the Platinum Group metals, especially platinum, rhodium, palladium, rhenium, as well as tungsten, gold, silver, tantalum, and alloys of these metals. These metals have significant radiopacity and their alloys may be tailored to accomplish an appropriate blend of flexibility and stiffness. They are also largely biologically inert. Additional coating materials, such as polymer, or biodegradable materials as discussed previously, may be added to the surface of the vaso-occlusive member 12 to improve the thrombogenic properties of the vaso-occlusive device.

The vaso-occlusive member 12 may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the entirety of which is hereby incorporated by reference.

Titanium/nickel alloy known as "nitinol" may also be used in the vaso-occlusive member 12. These are super-elastic and very sturdy alloys that will tolerate significant flexing without deformation even when used as a very small diameter wire. If nitinol is used in the device, the diameter of the vaso-occlusive member 12 may be significantly smaller than that of a vaso-occlusive member 12 that uses the relatively more ductile platinum or platinum/tungsten alloy as the material of construction.

The vaso-occlusive member 12 may also be made of radiolucent fibers or polymers (or metallic threads coated with radiolucent or radiopaque fibers) such as Dacron (polyester), polyglycolic acid, polylactic acid, fluoropolymers (polytetrafluoroethylene), Nylon (polyamide), or even silk.

As illustrated in FIGS. 1–6, the key-way(s) 14 can be variously configured on the vaso-occlusive member 12. There are a number of methods for creating the key-way(s) 14 along the vaso-occlusive member 12. For examples, the key-way(s) 14 may be created by laser-etching or by mechanical removal of a portion of the vaso-occlusive member 12. The key-way(s) 14 may also be created during the fabrication of the vaso-occlusive member 12. Heat may also be used to shape the key-way(s) 14 in the vaso-occlusive member 12.

Referring specifically to FIG. 1, one variation of a vaso-occlusive device 10(1) includes a key-way 14a, which takes the form of a pitched slot or groove that is created along a portion of the vaso-occlusive member 12. As illustrated, the key-way 14a may vary its pitch along the length of the vaso-occlusive member 12. Alternatively, the key-way 14a may have a constant pitch along the length of the vaso-occlusive member 12. If the pitch of the key-way 14a varies along the length of the vaso-occlusive member 12, it may be randomly selected or it may be in a pre-determined pattern.

Figure 1A:
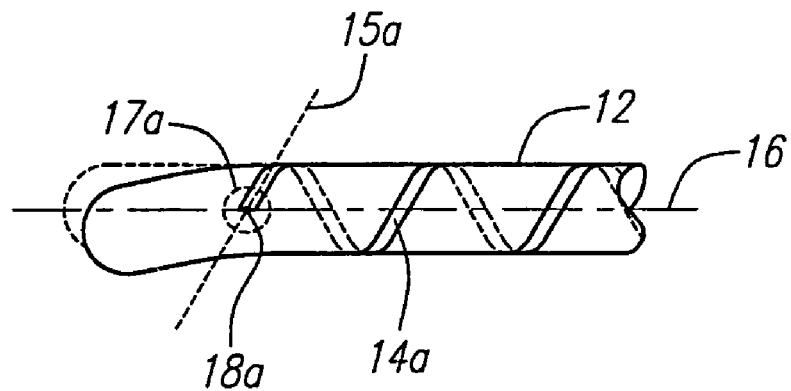
FIGS. 1A and 1B are side views of the foldable vaso-occlusive device of FIG. 1 when the device is folded along two different points, respectively, along the vaso-occlusive device.
Figure 1B:
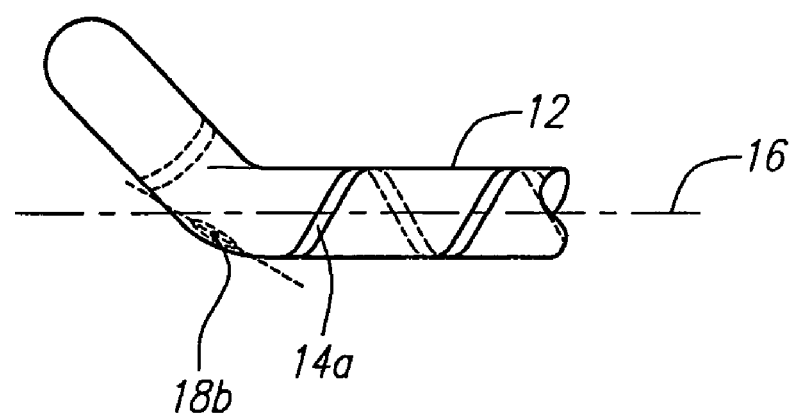

As shown in FIG. 1, the key-way 14a is disposed continuously along a portion of the vaso-occlusive member 12. The key-way 14a weakens the cross section of the vaso-occlusive member 12 and makes the vaso-occlusive member 12 more susceptible to folding along the key-way 14a when the vaso-occlusive member 12 is subjected to an external force. The direction of the fold lines depends on the direction of the pitch of the portion of the key-way 14a subject to folding. FIG. 1 shows two possible fold lines 15a and 15b, along which the vaso-occlusive member 12 could fold. Fold line 15a, which coincides with the pitch of the key-way 14a at one point 18a along the vaso-occlusive member 12, is at an angle 17a with an axis 16 of the vaso-occlusive member 12. Similarly, fold line 15b, which coincides with the pitch of the key-way 14a at a different point 18b along the vaso-occlusive member 12, is at an angle 17b with the axis 16 of the vaso-occlusive member 12. FIG. 1A shows a folded configuration of the vaso-occlusive device 10(1) when the vaso-occlusive member 12 folds along the key-way 14a at point 18a. FIG. 1B shows another folded configuration of the vaso-occlusive device 10(1) when the vaso-occlusive member 12 folds along the key-way 14a at point 18b. As shown in FIGS. 1A and 1B, the direction of the fold lines is the same as the direction of the pitch of the key-way 14a at a particular point along the vaso-occlusive member 12. It should be noted that points 18a and 18b are exemplary positions along the vaso-occlusive member 12 at which the member 12 could fold. Because the key-way 14a are disposed continuously along the vaso-occlusive device 10(1), the folding of the vaso-occlusive member 12 could occur anywhere along the vaso-occlusive device 10(1), and the folding direction would be based on the pitch of the key-way 14a at the location of the folding, as discussed previously. As such, for the purpose of this specification, key-way that is "disposed continuously along the vaso-occlusive device" refers to key-way which allows the folding of the vaso-occlusive member to occur at more than one location along the vaso-occlusive device.

FIG. 1 also shows a region 19 in which the pitch of the key-way 14a are is relative tight. In general, the more material removed per unit length at a portion along the vaso-occlusive member 12, the weaker the section at the corresponding portion of the vaso-occlusive member 12. As such, region 19 of the vaso-occlusive device 10(1) is relatively weaker than the rest of the device 10(1), and therefore, more susceptible to folding.

Figure 2:
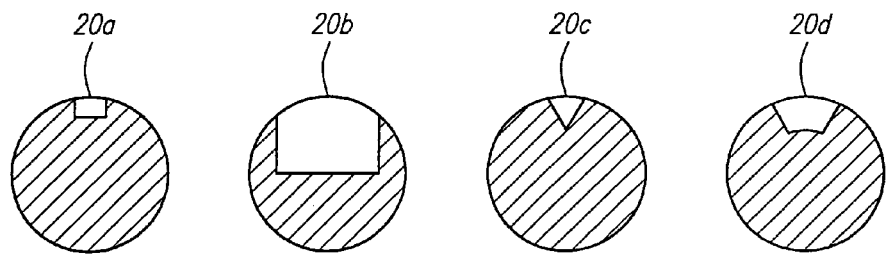
FIG. 2 are cross-sectional views of the key-way employed within the vaso-occlusive device of FIG. 1.

FIG. 2 shows variations of the cross-section 20 of the vaso-occlusive member 12. For example, cross-section 20a of the vaso-occlusive member 12 has a key-way 14a that is substantially rectangular in cross-section. Cross-section 20b has a key-way 14a that is of a different dimension from tat of cross-section 15. Cross-section 20c has a key-way 14a that is substantially triangular in cross-section. Cross-section 20d has a key-way 14a that is substantially trapezoidal in cross-section. The cross-sectional shape of the key-way 14a is not limited to that shown in FIG. 2. Other cross-sectional shapes may also be used for the key-way 14a.

Figure 3:
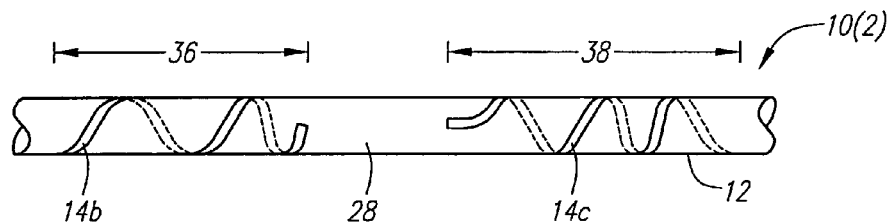
FIG. 3 is a side view of another variation of a foldable vaso-occlusive device constructed in accordance the first preferred embodiment of the present inventions, particularly showing two pitched key-ways axially separated from each other.

In the embodiment shown in FIG. 1, the vaso-occlusive device 10(1) has a single key-way 14a. More than one key-way 14, however, may be included on a vaso-occlusive device. For example, FIG. 3 illustrates a variation of a vaso-occlusive device 10(2), which includes key-ways 14b and 14c along portions of the length of the member 12. As shown in FIG. 3, the key-ways are axially spaced from each other, creating a spacing that separates the key-ways 14. Although only two key-ways 14 are shown, the rest of the length of the vaso-occlusive member 12 may include additional key-ways that are spaced apart in a similar fashion. The spacing of the key-ways 14 along the vaso-occlusive member 12 may also vary along the length of the vaso-occlusive member 12. The key-ways 14 may have various cross-sectional shapes and dimensions as discussed previously. Furthermore, the pitch of either one of key-ways 14 may be uniform, or may vary randomly or in a pre-selected manner. Because the region 28 has no key-way, the vaso-occlusive device 10(2) will more easily fold along portions 36 and 38 of the vaso-occlusive member 12. Furthermore, because the key-ways 14 are disposed continuously along the portions 36 and 38 of the vaso-occlusive member 12, the vaso-occlusive member 12 will fold at any location along the portions 36 and 38 of the vaso-occlusive member 12, and the folding direction at a given point along the vaso-occlusive member 12 would be based on the pitch of the key-ways 14, as discussed previously. If a more accurate folding location along the vaso-occlusive device 10(2) is desired, the extent of the key-ways along the vaso-occlusive member 12 may be shortened i.e., decreasing the dimensions of the portions 36 and 38, thereby, confining the regions along the vaso-occlusive member 12 in which the folding occurs.

Figure 4:
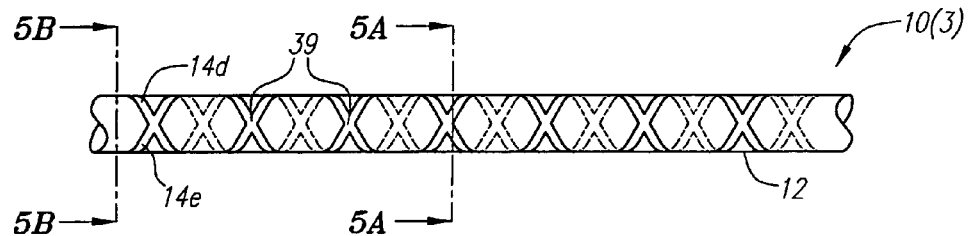
FIG. 4 is a side view of still another variation of a foldable vaso-occlusive device constructed in accordance the first preferred embodiment of the present inventions, particularly showing two pitched key-ways intersecting each other.
Figure 5A:
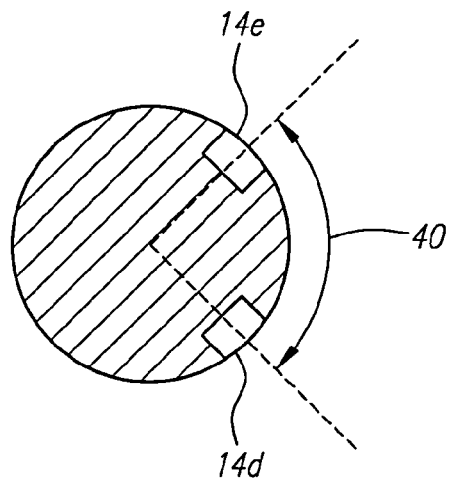
FIGS. 5A and 5B are cross-sectional views of the vaso-occlusive device of FIG. 4 taken along the lines 5A—5A and 5B—5B.
Figure 5B:
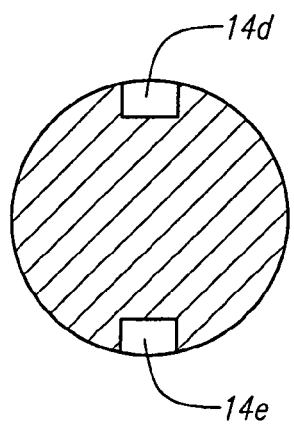

As another example, FIG. 4 illustrates another variation of a vaso-occlusive device 10(3). The vaso-occlusive device 10(3) includes key-ways 14*d* and 14*e* along a portion of the length of the vaso-occlusive member 12. The key-way 14*d* intersects the key-way 14*e* at various points 39 along the vaso-occlusive member 12. FIG. 5A shows another cross-section of the vaso-occlusive device 10(3) taken at a different point along the length of the device 10(3), in which the key-way 14*d* is at an angle 40 from the key-way 14*e*. FIG. 5B shows a cross-section of the vaso-occlusive device 10(3), in which the key-way 14*d* is directly opposite from the key-way 14*e*.

Figure 6:
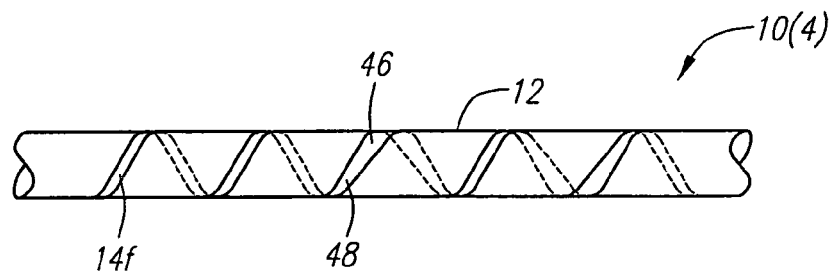
FIG. 6 is a side view of still another variation of a foldable vaso-occlusive device constructed in accordance the first preferred embodiment of the present inventions, particularly showing a pitched key-way that varies in dimension and/or shape.

In the previous embodiments, the key-ways 14 exhibit uniform widths along their lengths. The widths of the key-ways 14, however, can vary along the length of the vaso-occlusive member 12. For example, FIG. 6 illustrates a variation of a vaso-occlusive device 10(4). The device 10(4) includes a key-way 14*f* that varies in width along the length of the member 12. The key-way 14 is wider at portion 46 of the device 10(4) than at portion 48 of the device 10(4). The wider or deeper the key-way at a particular location along the vaso-occlusive member 12, the weaker is the cross section at that location, and therefore, the more likely that the vaso-occlusive member 12 would fold at that location.

Figure 7:
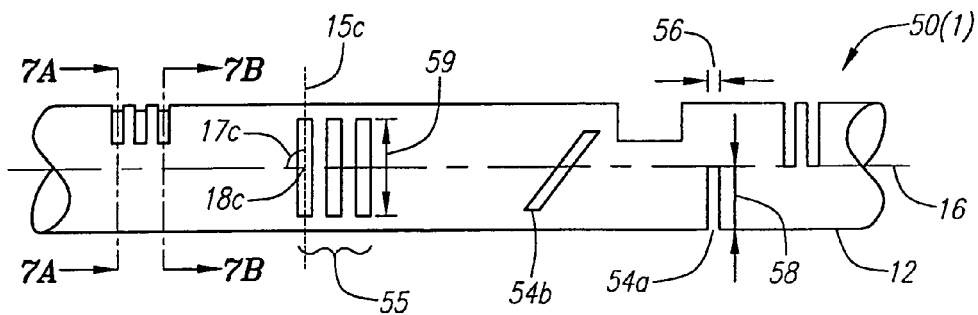
FIG. 7 is a side view of one variation of a foldable vaso-occlusive device constructed in accordance with a second preferred embodiment of the present inventions, particularly showing key-ways that are disposed discretely along the vaso-occlusive device and are partially disposed about a portion of the circumference of the vaso-occlusive device.
Figure 8:
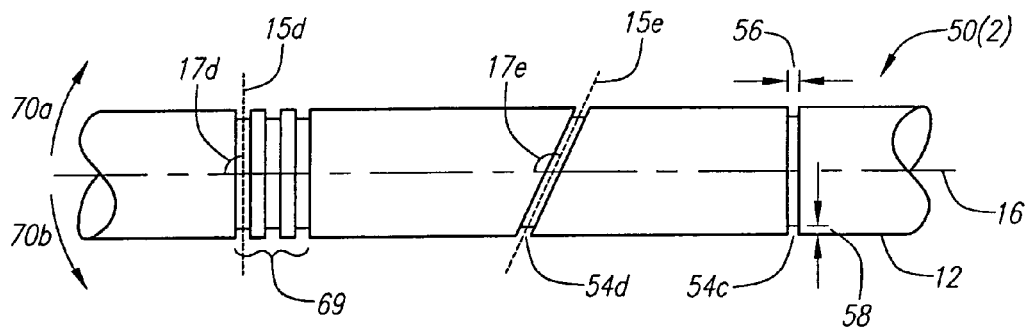
FIG. 8 is a side view of another variation of a foldable vaso-occlusive device constructed in accordance with the second preferred embodiment of the present inventions, particularly showing key-ways that are disposed discretely along the vaso-occlusive device and are disposed completely around the circumference of the device.

Unlike the vaso-occlusive device shown previously in FIGS. 1–6, wherein the key-ways 14 are disposed continuously along portion(s) of the member 12, FIGS. 7–8 illustrate various alternative preferred embodiments of vaso-occlusive devices 50 having key-ways 54 that are not disposed continuously along portion(s) of the vaso-occlusive member 12. In particular, the key-ways 54 are disposed discretely along the vaso-occlusive member 12 and are circumferentially disposed about the perimeter of the vaso-occlusive member 12. As such, the key-ways 54 provide a defined and more predictable location at which the vaso-occlusive member 12 could fold. For the purpose of this specification, key-way that is "disposed discretely along the vaso-occlusive device" refers to key-way for which the folding of the vaso-occlusive member occurs at only one location along the vaso-occlusive device. The key-ways 54 are defined by slots or grooves that can be formed within the member 12 in any of a variety of manners and exhibit any of a variety of cross-sections. The key-way 54 may have a variety of geometric shapes or irregular shapes, as described previously. In the embodiments illustrated in FIGS. 7 and 8, the key-ways 54 are defined rectangular slots, each of which has a width 56 and a depth 58.

Figure 7A:
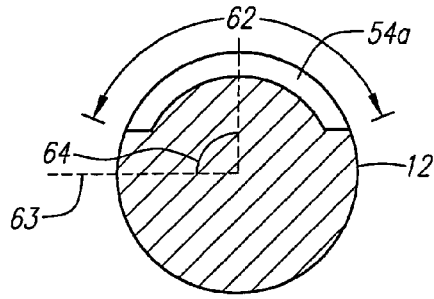
Figure 7B:
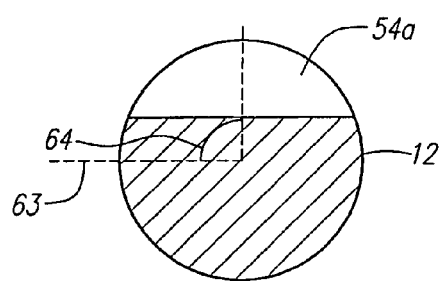

Referring specifically to FIG. 7, one variation of a vaso-occlusive device 50(1) includes key-ways 54*a* partially disposed about a portion 62 of the circumference of the member 12. Such a configuration has the benefit of providing directionality because the vaso-occlusive member 12 will tend to bend in the direction towards the key-way 54*a*. The key-ways 54*a* may conform with the shape of the vaso-occlusive member 12 as shown in FIG. 7A. Alternatively, as shown in FIG. 7B, the key-ways 54*a* may completely penetrate through a portion of the section of the vaso-occlusive member 12. As shown in FIGS. 7A and 7B, each of the key-ways 54*a* is radially oriented at an angle 64 relative to a reference radial axis 63.

As shown in FIG. 7, the fold line 15*c* of the vaso-occlusive device 50(1) at point 18*c* along the vaso-occlusive member 12 is at an angle 17*c* that is perpendicular to the axis 16 of the vaso-occlusive member 12. As such, the folding direction of the vaso-occlusive member 12 at point 18*c* would be perpendicular to the axis 16. The vaso-occlusive device 50(1) may also have key-way(s) 54*b* that exhibits a pitch for providing a desired orientation of the fold line. Furthermore, the key-ways 54*a* may be disposed about the circumference of the vaso-occlusive member 12 at different radial angles 64 relative to the reference radial axis 63 (see FIG. 7A) such that the vaso-occlusive member 12 may fold at different radial angles at different points along the vaso-occlusive member 12. The key-ways 54*a* may be formed in groups 55 at different portions along the length of the vaso-occlusive member 12. The number of key-ways 54*a* in each group 55 may vary. Increasing the number of key-ways 54 in a group 55 has the effect of lowering the axial and bending strength of the vaso-occlusive member 12 at the corresponding section of the member 12, and therefore, making it easier for the vaso-occlusive member 12 to fold at that section.

Rather than provide a predictable folding direction relative to a reference radial axis (i.e., axis 63 in FIG. 7A), the device can be made to fold in a non-predetermined direction. For example, FIG. 8 illustrates a variation of a vaso-occlusive device 50(2) that includes key-ways 54*c* disposed completely around the circumference of the vaso-occlusive member 12, such that the cross-section of the vaso-occlusive member 12 at the location of the key-way 54*c* is symmetric about the axis 16 of the vaso-occlusive member 12. This configuration provides weakened axial and bending stiffness of the vaso-occlusive member 12 without directionality. That is, the vaso-occlusive member 12 would fold along the key-way 54*c* at an angle (i.e., 17*d* and 17*e*) that coincides with the pitch of the key-way 54*c*, but the folding direction (e.g. 70*a* and 70*b*) relative to the reference radial axis 63 is unpredictable. The vaso-occlusive device 50(2) may have key-way(s) 54*d* that exhibit a pitch. The vaso-occlusive device 50(2) may also have a different number of key-ways 54*b* in a group 69 at different portions along the length of the vaso-occlusive member 12 to further weaken the axial and bending stiffness at the corresponding portions, as discussed previously.

Figure 9:
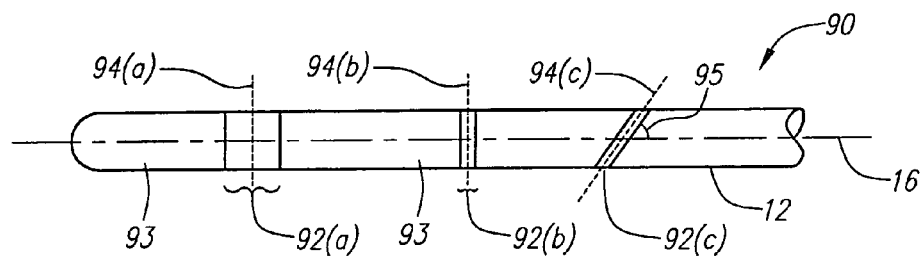
FIG. 9 is a side view of a foldable vaso-occlusive device constructed in accordance with a fourth preferred embodiment of the present inventions, particularly showing a vaso-occlusive member made of different materials along the length of the vaso-occlusive member.

Each of the foldable vaso-occlusive devices described so far includes at least one key-way for promoting specific folding configuration of the vaso-occlusive device. However, the folding configuration of the vaso-occlusive device may also be promoted by other methods. FIG. 9 illustrates an alternative preferred embodiment of a vaso-occlusive device 90 in which a portion 92 along the length of the vaso-occlusive member 12 is made of a material that is different from the adjacent regions 93 of the vaso-occlusive member 12. In particular, the portion 92 is preferably made of a material that is more flexible or weaker than that of the regions 93 of the member 12. The portion 92 may be secured to the adjacent regions 93 by glue or weld, for examples, depending upon the materials from which the portion 92 and the regions 93 are made. The length of the portion 92 along the vaso-occlusive device 90 may vary (See 92(a) and 92(b) in FIG. 9). The portion 92 may also form an angle 95 with an axis 16 of the vaso-occlusive device 90. When the vaso-occlusive device 90 is subjected to an external force or pressure, the relatively weaker portion 92 along the device 90 makes the vaso-occlusive member 12 more susceptible to folding or bending at the portion 92, and therefore, fold or bend along a fold line 94 at the corresponding portion 92.

Each of the vaso-occlusive devices described so far does not have a secondary or tertiary relaxed configuration. That is, the previously described vaso-occlusive devices have substantially rectilinear or a curvilinear (slightly curved, i.e. having less than 360° spiral) relaxed configurations. These vaso-occlusive devices only assume folded configurations when they are subjected to external forces, e.g., compressive forces when they encounter objects. As such, the key-way(s) (or the relatively weaker portion(s) of the vaso-occlusive member) facilitates the space-filling capacity (i.e., the ability to occupy a space uniformly with a given amount of material) of the vaso-occlusive device when introduced into the desired body cavity to be occluded even though the vaso-occlusive device does not assume a secondary or tertiary relaxed configuration. For the purposes of the following discussion, the term "relaxed configuration" refers to the shape of the vaso-occlusive device when it is outside a delivery catheter, or when it is not subjected to an external force. The term "folded configuration" refers to the shape of the vaso-occlusive device when the vaso-occlusive device folds along one or more of the desired fold lines.

Each of the key-ways described in FIGS. 1–8 and the configuration shown in FIG. 9 may also be incorporated into vaso-occlusive devices that assume a variety of secondary and tertiary relaxed configurations. The space-filling capacity of these vaso-occlusive devices is inherent within the secondary or tertiary relaxed shapes of these devices. When vaso-occlusive devices having secondary and/or tertiary relaxed configurations incorporate the key-way described herein, the devices conform better to the shape of the space being occluded and their space-filling capacity is improved due to the folded configuration resulting from the key-way, as will be discussed below.

Figure 10A:
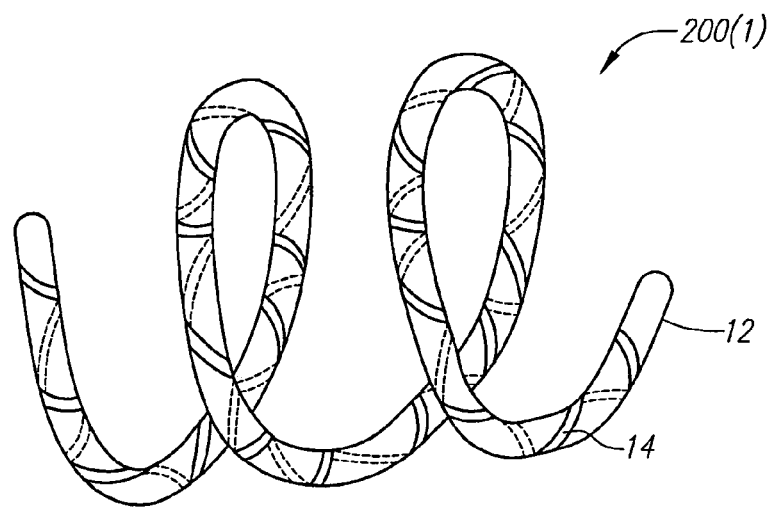
FIG. 10A is a side view of a variation of a foldable vaso-occlusive device constructed in accordance with a third preferred embodiment of the present inventions, particularly showing device having a helical secondary shape.
Figure 10B:
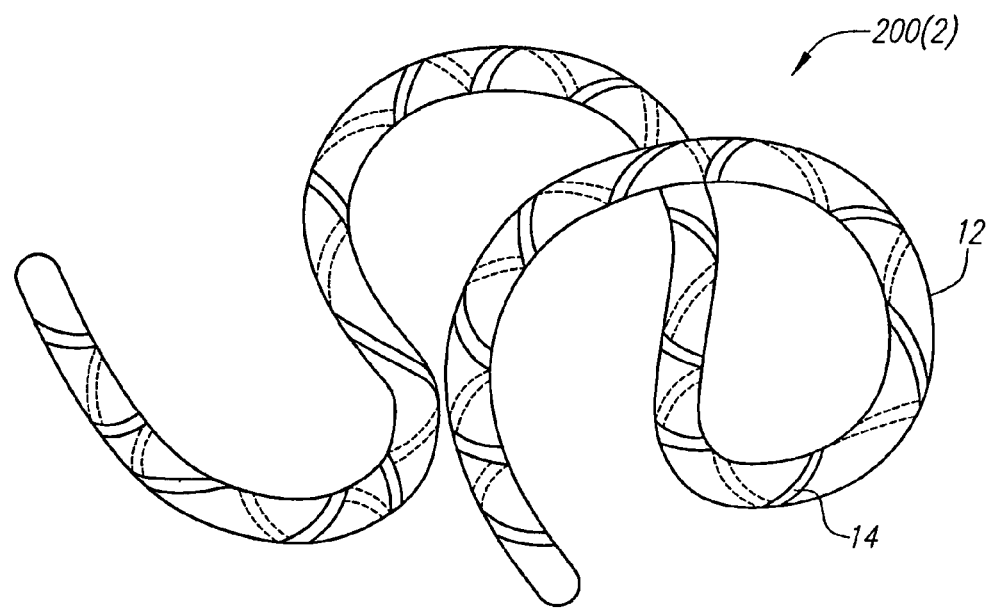
FIG. 10B is a side view of another variation of a foldable vaso-occlusive device constructed in accordance with the third preferred embodiment of the present inventions, particularly showing device having an irregular secondary shape.

FIGS. 10A and 10B illustrates vaso-occlusive devices 200 having secondary shapes. These shapes are simply indicative of the various secondary shapes that may be used, and other shapes may be used as well. The devices 200 illustrated in each of the FIGS. 10A and 10B may incorporate any variety of the key-ways, and may have portion(s) of the vaso-occlusive member made of a relatively weaker material, as discussed previously.

FIG. 10A depicts a vaso-occlusive device 200(1) having a secondary shape of a helical coil. FIG. 10B illustrates a vaso-occlusive device 200(2) having a random secondary shape. Each of the secondary shapes shown in FIGS. 10A and 10B may be achieved by wrapping a vaso-occlusive member 12 having a primary shape that is substantially linear, such as that shown in FIG. 1, around a mandrel, stylet, or other shaping element. The device 200 may be, but is not necessarily, subjected to a heating step as known to one skilled in the art to set the device into a secondary shape. It should be noted that the formation of vaso-occlusive devices into secondary shapes is well known in the art, and need not be described in further detail.

FIGS. 11–17 illustrate various vaso-occlusive devices 300 of this invention having a secondary shape of a helical coil, such as that shown in FIG. 10A, and a tertiary shape. These shapes are simply indicative of the various tertiary shapes that may be used, and other shapes may be used as well. While not shown, the devices 300 illustrated in each of the FIGS. 11–17 may incorporate the key-ways, as discussed previously. The devices 300 may also have portion(s) of the vaso-occlusive member made of a relatively weaker material, as also discussed previously.

Figure 11:
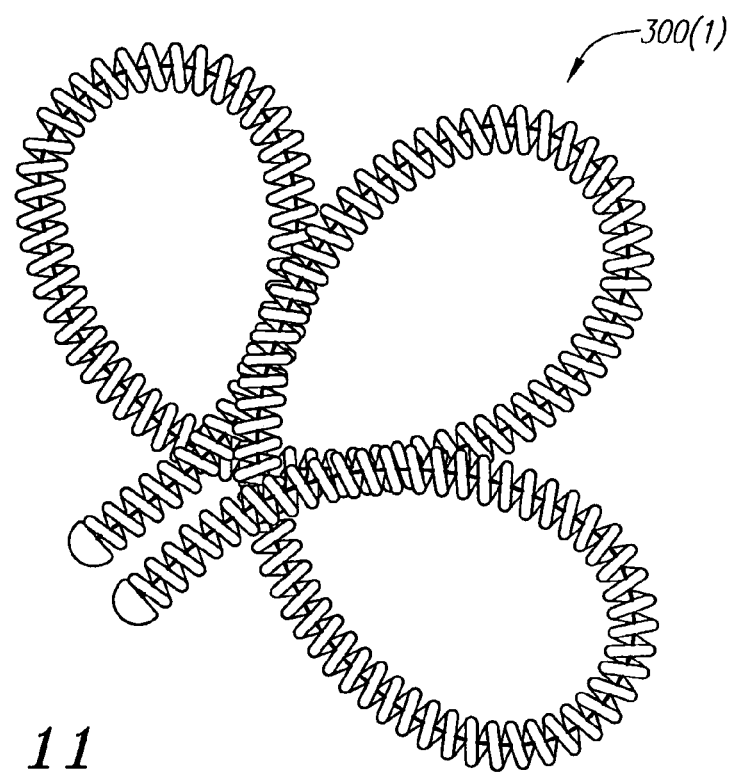
FIG. 11 is a side view of a variation of a foldable vaso-occlusive device constructed in accordance with a fourth preferred embodiment of the present inventions, particularly showing device having a clover leaf tertiary shape.
Figure 12:
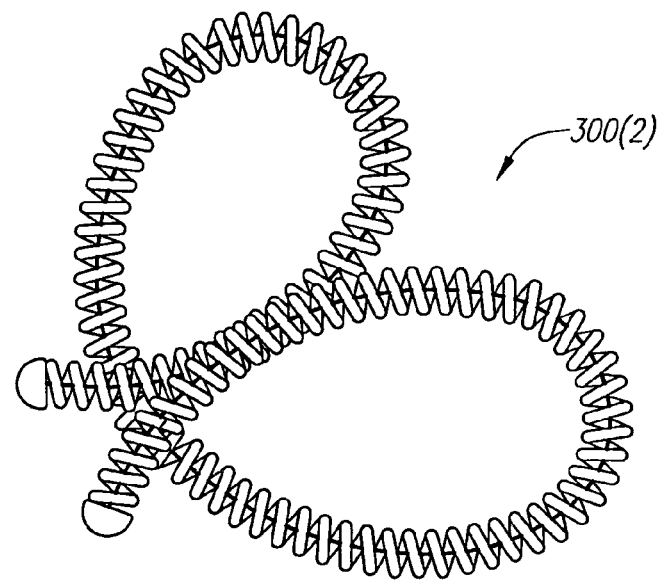
FIG. 12 is a side view of another variation of a foldable vaso-occlusive device constructed in accordance with the fourth preferred embodiment of the present inventions, particularly showing device having a twisted figure-8 tertiary shape.

FIG. 11 depicts a device 300(1) having a tertiary shape of a clover leaf. FIG. 12 depicts a device 300(2) having a tertiary shape of a twisted figure-8.

Figure 13:
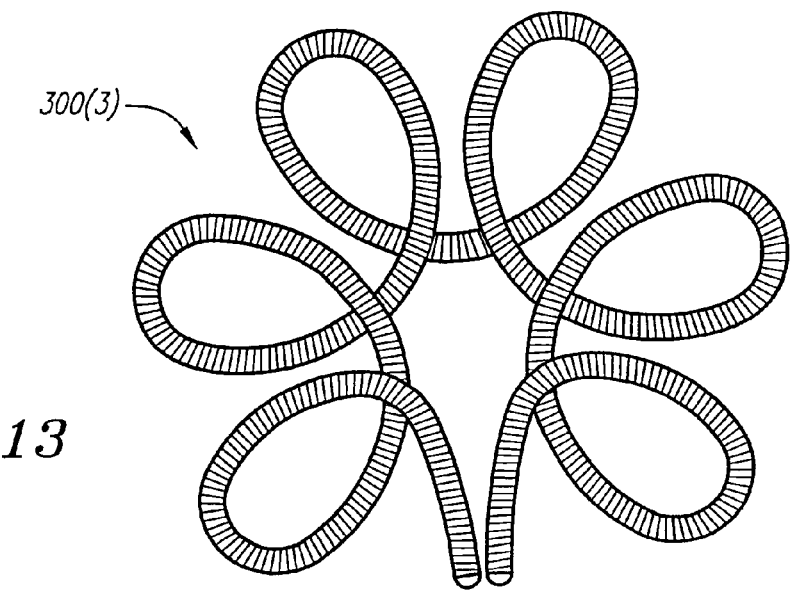
FIG. 13 is a side view of a still another variation of foldable vaso-occlusive device constructed in accordance with the fourth preferred embodiment of the present inventions, particularly showing device having a flower-like tertiary shape.
Figure 14:
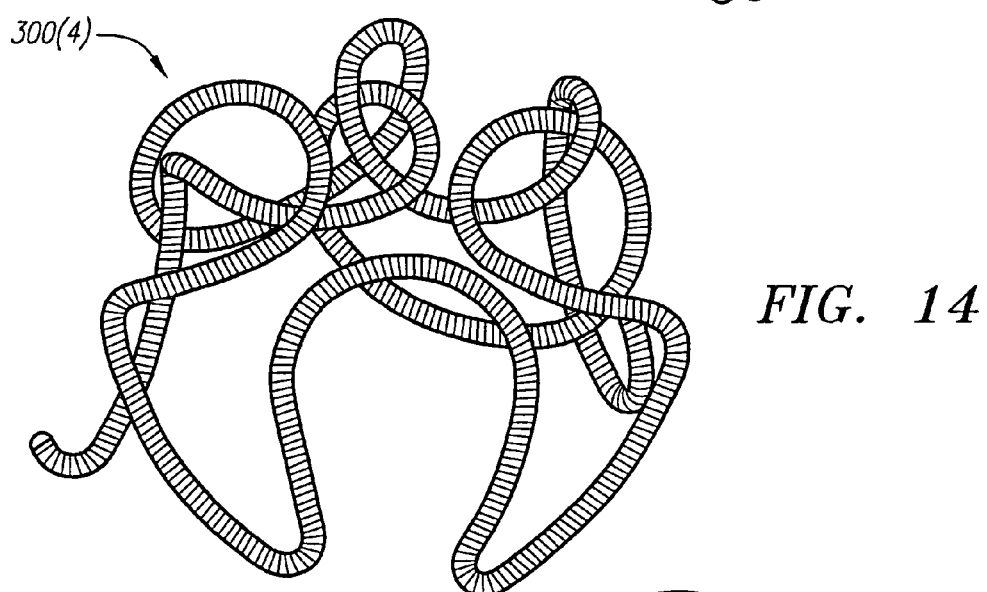
FIG. 14 is a side view of still another variation of a foldable vaso-occlusive device constructed in accordance with the fourth preferred embodiment of the present inventions, particularly showing device having a spherical tertiary shape.
Figure 15:
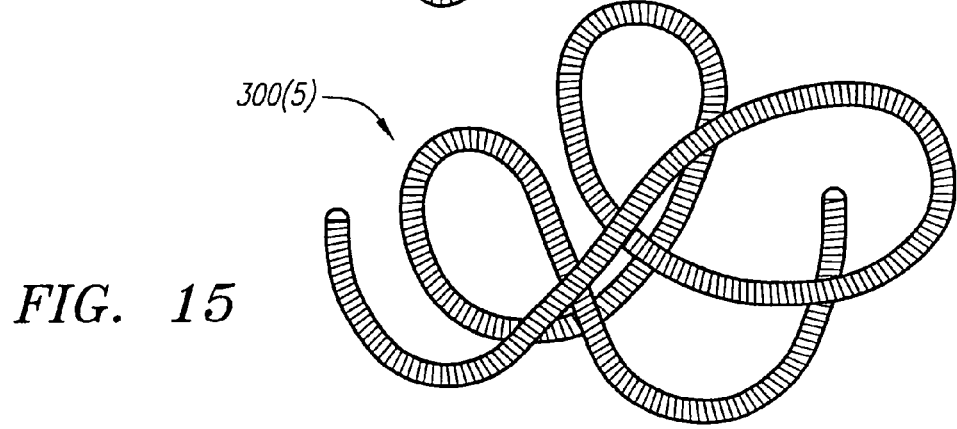
FIG. 15 is a side view of still another variation of a foldable vaso-occlusive device constructed in accordance with the fourth preferred embodiment of the present inventions, particularly showing device having a random tertiary shape.
Figure 16:
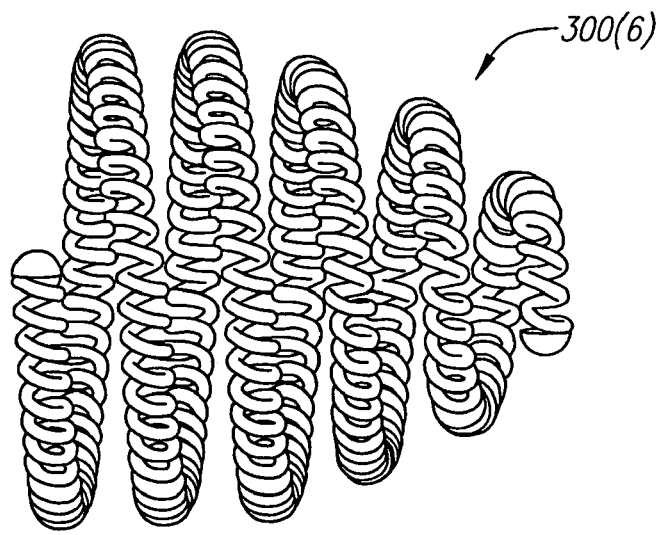
FIG. 16 is a side view of still another variation of a foldable vaso-occlusive device constructed in accordance with the fourth preferred embodiment of the present inventions, particularly showing device having a vortical tertiary shape.
Figure 17:
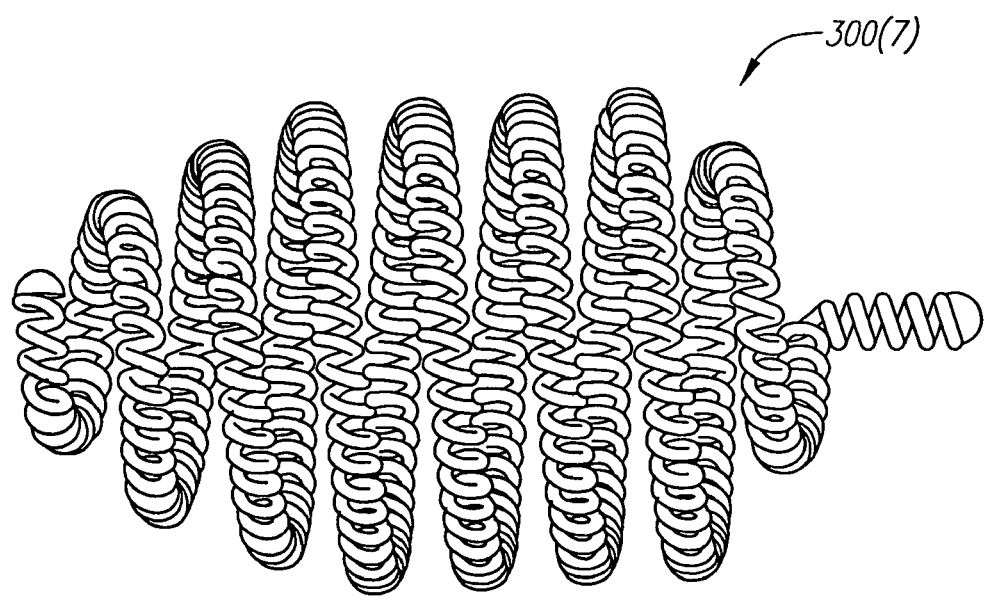
FIG. 17 is a side view of still another variation of a foldable vaso-occlusive device constructed in accordance with the fourth preferred embodiment of the present inventions, particularly showing device having an ovoidal tertiary shape.
Figure 18:
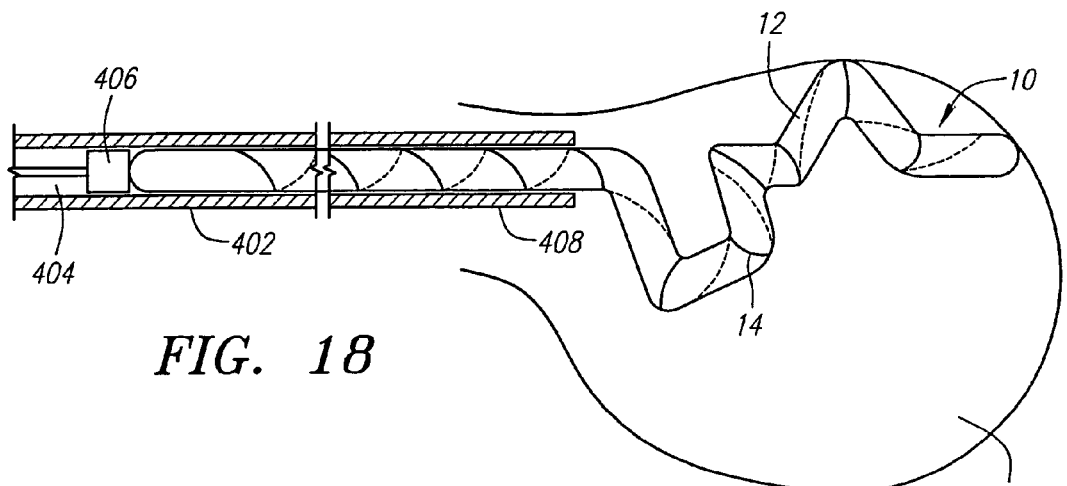
FIG. 18 is a side view of the first preferred embodiment of the foldable vaso-occlusive device being delivered within a body cavity using a delivery catheter.

FIG. 13 depicts a device 300(3) having a flower-shaped tertiary shape. FIG. 14 depicts a device 300(4) having a substantially spherical tertiary shape. FIG. 15 illustrates a device 300(5) having a random tertiary shape. FIG. 16 illustrates a device 300(6) having tertiary shape of a vortex. FIG. 17 illustrates a device 300(7) having a tertiary shape of an ovoid.

To make the tertiary shaped vaso-occlusive devices 300, a vaso-occlusive member 12 having a primary shape that is substantially rectilinear or curvilinear is first wrapped around a mandrel or other shaping element to form a secondary shape, such as the helical coil shown in FIG. 10A. The mandrel and the vaso-occlusive member 12 may be heated to shape the vaso-occlusive member 12 into the secondary shape. The secondary shaped vaso-occlusive member, or as in the case for the devices shown in FIGS. 11–17, the helical coil, is then wrapped around another shaping element to produce the tertiary shape. Heat may also be used to shape the vaso-occlusive member 12 to form the tertiary shape. Stable coil designs, and methods of making such, are described in U.S. Pat. No. 6,322,576B1 to Wallace et al., the entirety of which is incorporated by reference herein. It should be noted that the formation of vaso-occlusive devices into tertiary shapes is well known in the art, and need not be described in further detail.

The method of using the previously described vaso-occlusive devices will now be discussed with reference to FIGS. 18–21. It should be noted that although the method is described with reference to foldable vaso-occlusive devices having key-way(s), the method is also appropriate for other foldable vaso-occlusive devices described previously.

First, a delivery catheter 402 is inserted into the body of a patient. Typically, this would be through a femoral artery in the groin. Other entry sites sometimes chosen are found in the neck and are in general well known by physicians who practice these types of medical procedures. The delivery catheter 402, which may be a microcatheter for example, is positioned so that the distal tip 408 of the delivery catheter 402 is appropriately situated, e.g., within the mouth of the body cavity 401 to be treated. The insertion of the delivery catheter 402 may be facilitated by the use of a guidewire and/or a guiding catheter, as is known in the art. In addition, the movement of the catheter 402 may be monitored fluoroscopically.

Once the delivery catheter 402 is in place, a vaso-occlusive device, and in this case the vaso-occlusive device 10, is then inserted from the proximal end (not shown) of the delivery device 402, and into the lumen of the delivery device 402. Since the vaso-occlusive device 10 has no secondary or tertiary relaxed configuration, the vaso-occlusive device 10 would naturally assume a substantially rectilinear or a curvilinear configuration when disposed within the lumen of the delivery device 402, without being subjected to substantial stress.

Figure 19:
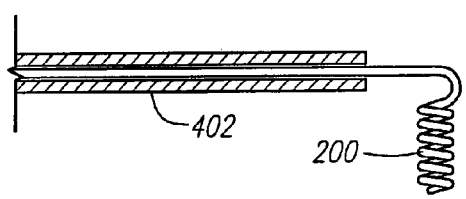
FIG. 19 is a side view of the third preferred embodiment of the foldable vaso-occlusive device being delivered using a delivery catheter, particularly showing the stretching of the secondary shape of the vaso-occlusive device into a linear form within the delivery catheter.

For vaso-occlusive devices having secondary shape or tertiary shapes, such as the vaso-occlusive devices 200 and 300 shown in FIGS. 10–17, they may be "stretched" to a substantially linear shape while residing within the lumen of the delivery catheter 402, as illustrated with the vaso-occlusive device 200 in FIG. 19. The advantage of having the vaso-occlusive devices 200 and 300 assume a linear shape within the delivery device 402 is that the cross-sectional dimension of the delivery catheter 402 can be made much smaller, which in turn, assists the insertion of the catheter 402 into the body of a patient and improves the maneuverability of the catheter 402 within the body.

Figure 20:
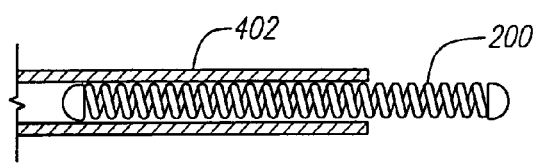
FIG. 20 is a side view of the third preferred embodiment of the foldable vaso-occlusive device being delivered using a delivery catheter, particularly showing the maintaining the natural secondary shape of the vaso-occlusive device.
Figure 21:
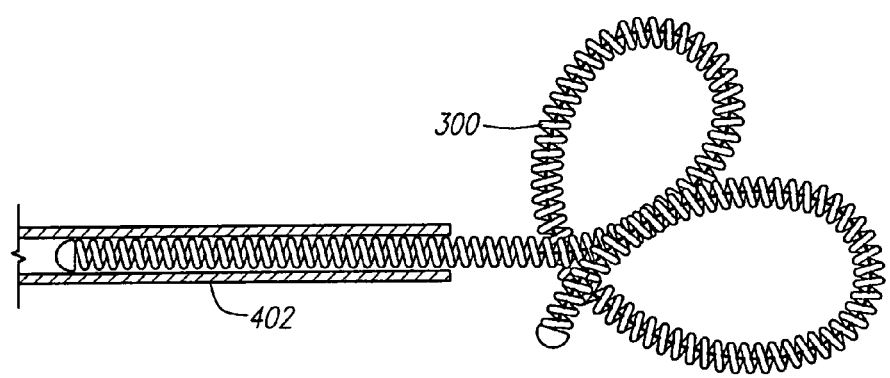
FIG. 21 is a side view of the fourth preferred embodiment of the foldable vaso-occlusive device being delivered using a delivery catheter, particularly showing the stretching of the tertiary shape of the vaso-occlusive device into a secondary shape within the delivery catheter.

Alternatively, as shown in FIG. 20, a vaso-occlusive device having a secondary shape of a helical coil, such as the vaso-occlusive device 200, may be disposed within the lumen of a deliver catheter in its unstretched configuration. Furthermore, as shown in FIG. 21, a vaso-occlusive device having a tertiary shape made of a helical coil, such as the vaso-occlusive device 300, may be "stretched" to its secondary shape, in the form of a substantially linear helical coil, when disposed within the lumen of a delivery catheter 402.

Referring back to FIG. 18, the vaso-occlusive device 10 is preferably advanced distally towards the distal end 408 of the delivery catheter 402 with the use of a wire 404. A plunger 406 may be attached to the distal end of the wire 404 to assist advancement of the vaso-occlusive device 10. Alternatively, fluid pressure may also be used to advance the vaso-occlusive device 10 along the delivery catheter 402. The inner diameter of the delivery catheter 402 should be made large enough to allow advancement of the vaso-occlusive device 10. On the other hand, the inner diameter of the delivery catheter 402 should not be significantly larger than the overall cross-sectional dimension of the vaso-occlusive device 10 in order to avoid bending and kinking of the vaso-occlusive device 10 within the lumen of the delivery catheter 402.

For a vaso-occlusive device having no secondary or tertiary relaxed configuration, the vaso-occlusive device would remain substantially rectilinear or curvilinear without undergoing substantial stress while residing within the lumen of the delivery catheter 402. Once the vaso-occlusive device 10 or a portion of the vaso-occlusive device 10 exits from the distal end 408 of the delivery catheter 402, it remains substantially rectilinear or curvilinear until it comes in contact with an object, i.e., the wall of the body cavity 401. If the vaso-occlusive device 10 is continued to be advanced towards the body cavity, the vaso-occlusive device 10 would be subjected to axial and/or bending stress due to the force/pressure exerted by the advancing force and by the object that it comes in contact with. As the result, the vaso-occlusive device 10 folds along one or more of the key-ways. As discussed previously, the folding pattern of the vaso-occlusive device 10 is promoted by the key-way(s) 14, which weaken the axial strength and flexural strength of the vaso-occlusive device 10 and produce one or more preferred fold lines in the device 10. When the vaso-occlusive device 10 is completely discharged from the delivery catheter 402, it should assume a three dimensional configuration within the body cavity 401.

For vaso-occlusive devices having secondary or tertiary shapes, the vaso-occlusive device would resume its relaxed configuration when ejected from the lumen of the delivery catheter 402. The shape of the secondary or tertiary relaxed configuration would help fill up the body cavity 401. Furthermore, the key-ways along portions of the vaso-occlusive member 12 allow the vaso-occlusive device to fold when portions of the vaso-occlusive device encounter the wall of the body cavity 401 or other object, as discussed previously. The folded configuration allows the vaso-occlusive device to better conform to the shape of the body cavity and helps fill up the body cavity more efficiently, which in turn, assists formation of thrombi within the body cavity.

Additional vaso-occlusive devices may also be placed within the body cavity 401 by repeating the relevant steps discussed above. When a desired number of vaso-occlusive devices have been placed within the body cavity 401, the delivery catheter 402 is then withdrawn from the body cavity 401. Once the vaso-occlusive devices are situated in the body cavity 401, an embolism then forms to occlude the body cavity 401.

Figure 22:
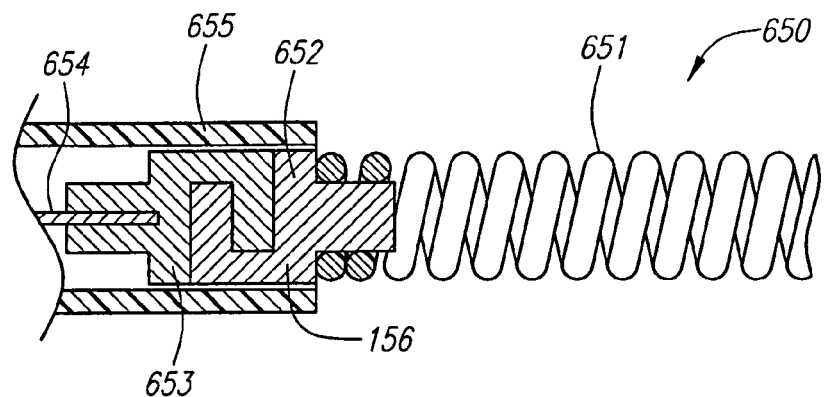
FIG. 22 is a side view of a portion of a delivery catheter in which the foldable vaso-occlusive device is adapted to be mechanically released from the distal end of a wire.

FIG. 22 depicts an embodiment, generally designated 650, having a vaso-occlusive device 651 that may be detached through operation of a connective joint 652. The vaso-occlusive device 651 may be any one of the devices depicted in FIGS. 1–17, and it includes one or more key-ways (not shown for clarity). Joint 652 has a clasp section 653 which remains attached to a core wire 654 when sheath or catheter body 655 is retracted proximally. Joint 652 also includes a second clasp section 656 that is carried on the proximal end of the vaso-occlusive device 651 and interlocks with clasp section 653 when the assembly is within sheath 655. When the sheath is withdrawn from about the assembly, the clasp sections are free to disengage, thus detaching coil 651. Core wire 651 may be electrically connected to a source of radiofrequency energy.

The vaso-occlusive devices described herein may also be nondetachable or detachable by electrolytic means such as described in U.S. Pat. Nos. 5,234,437, 5,250,071, 5,261,916, 5,304,195, 5,312,415, and 5,350,397.

Figure 23:
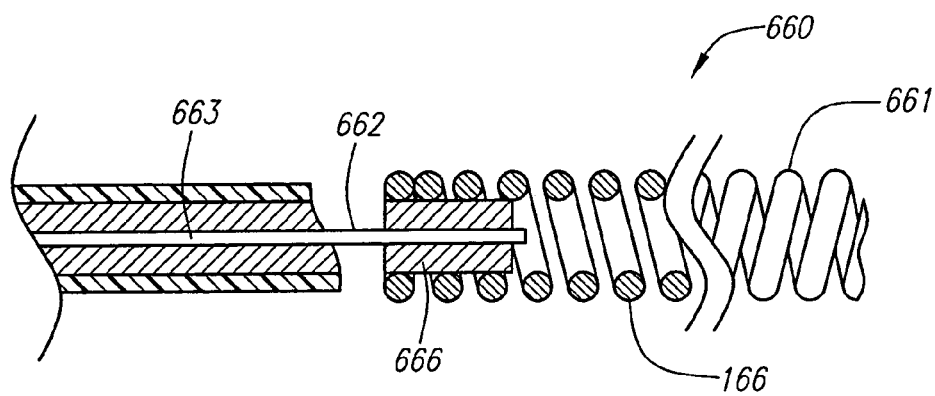
FIG. 23 is a side view of a portion of a delivery catheter in which the foldable vaso-occlusive device is adapted to be electrolytically released from the distal end of a wire.

FIG. 23 shows an embodiment, generally designated 660, having a vaso-occlusive device 661 that may be detached through operation of a connective joint 662 that is susceptible to electrolysis. The vaso-occlusive device 661 may be any one of the devices depicted in FIGS. 1–17, and it includes one or more key-ways (not shown for clarity). Such joints are described in detail in U.S. Pat. No. 5,423,829, which is incorporated by reference herein. Joint 662 is made of a metal which, upon application of a suitable voltage to a core wire 663, will erode in the bloodstream, thereby allowing the vaso-occlusive device 661 to detach. The vaso-occlusive device 661 is made of a metal that is more "noble" in the electromotive series than the metal of joint 662. A return electrode (not shown) is supplied to complete the circuit. The region of core wire 663 proximal to the joint is insulated to focus the erosion at the joint. An electrically conductive bushing 666 is used to connect the distal end of core wire 663 to the proximal end of the vaso-occlusive device 661.

Figure 24:
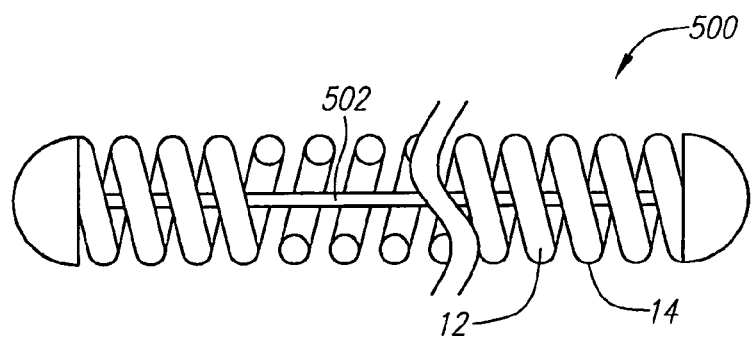
FIG. 24 shows a side view, partial cutaway of a foldable vaso-occlusive device having a fibrous stretch-resisting member.

It should be noted that the vaso-occlusive devices described herein may also incorporate other features. For example, any of the vaso-occlusive devices shown in FIGS. 9–17 may also include a stretch-resisting member to prevent the device from over-stretching. FIG. 24 illustrates a vaso-occlusive device 500 having a stretch-resisting member 502. The vaso-occlusive device 500 has a secondary shape of a helical coil and it includes the key-way 14 (not shown), as discussed previously. The stretch-resisting member 502 is preferably positioned coaxially within the lumen of a helical coil. However, the stretch-resisting member 502 may also be placed outside the lumen of the helical coil. As shown in FIG. 24, the stretch-resisting member 502 may be secured at the ends of the vaso-occlusive device 500. Alternatively, the stretch-resisting member 502 may be secured at any two points along the vaso-occlusive device 500. The stretch-resisting member 502 is preferably polymeric, and may be thermoplastic or thermosetting. In some instances, it may also be desirable to include one or more metallic strands in the stretch-resisting member 502 to provide stiffness or electrical conductance for specific applications. The stretch-resisting member 502 may also be a wire or "ribbon" which is soldered, brazed, glued, or otherwise fixedly attached to the ends of the vaso-occlusive device 500, or to the device 500 at one or more locations intermediate to those ends. Stretch-resisting members are described in U.S. Pat. No. 6,280,457 to Wallace et al., the entirety of which is incorporated by reference herein.

Figure 25:
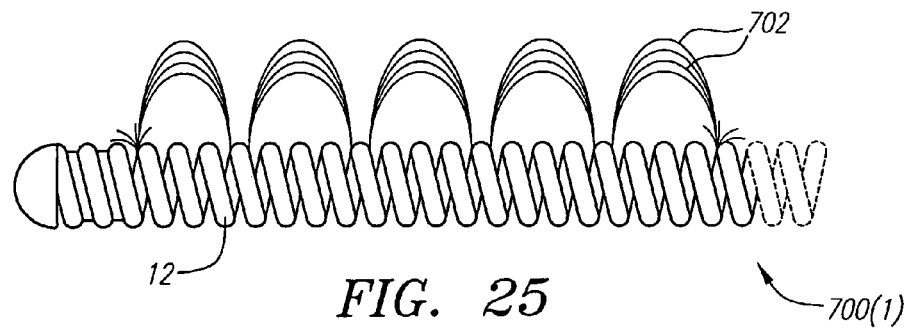
FIG. 25 shows a partial side view of a foldable vaso-occlusive device having plurality of fibers.
Figure 26:
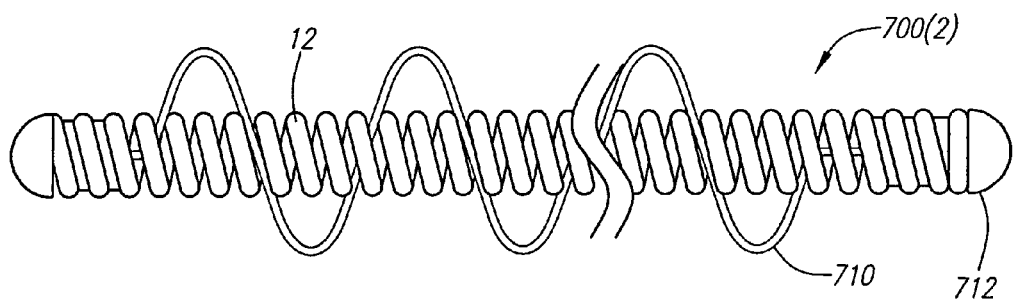
FIG. 26 shows a partial side view of a foldable vaso-occlusive device having a strand of polymer that extends sinusoidally along the length of the device.
Figure 27:
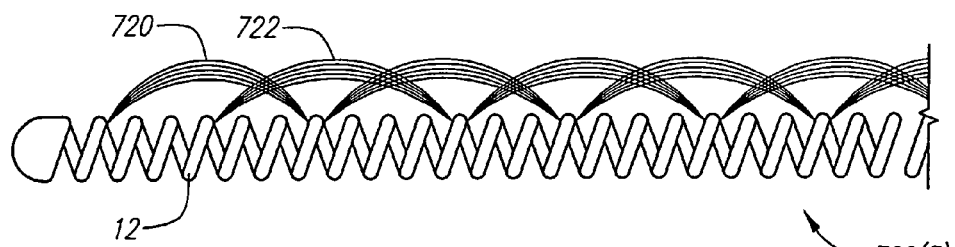
FIG. 27 shows a partial side view of a foldable vaso-occlusive device having multiple filamentary elements.
Figure 28:
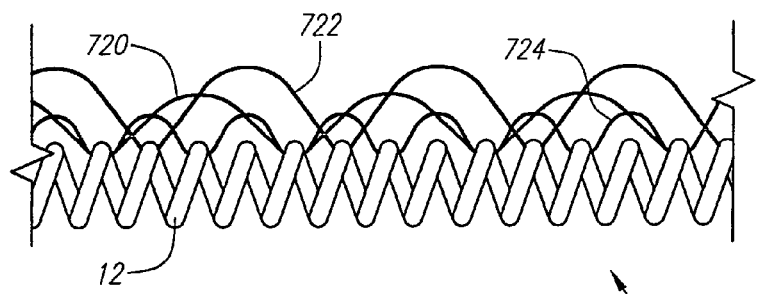
FIG. 28 shows a partial side view of a foldable vaso-occlusive device having multiple filamentary elements spaced at various intervals.

The vaso-occlusive devices 700 illustrated in FIGS. 25–28 include key-way(s) as described previously, which is not shown for clarity. As shown in FIG. 25, the vaso-occlusive device 700(1) may include one or more filamentary elements 702 attached to the coil windings to increase the overall thrombogenic properties of the device 700(1). FIG. 26 illustrates a vaso-occlusive device 700(2) having a strand of polymer 710 that extends sinusoidally along the length of the coil. The ends of the polymer 710 may be fused to and integral with the polymer tips 712. As shown, the strand of polymer 710 is composed of loops that extend radially outwardly of the coil windings and extend through the coil windings at spaced intervals. Furthermore, as shown in FIGS. 27 and 28, the vaso-occlusive devices 700(3) and 700(4) may also include multiple filamentary elements 720, 722, and 724, spaced at the same or different intervals, respectively, along the length of the vaso-occlusive device to increase the thrombogenic properties of the device.

Thus, although several preferred embodiments have been shown and described, it would be apparent to those skilled in the art that many changes and modifications may be made thereunto without the departing from the scope of the invention, which is defined by the following claims and their equivalents.

What is claimed is:

1. A vaso-occlusive device, comprising:
   an elongate vaso-occlusive member, the vaso-occlusive member capable of assuming a desired folded configuration when the vaso-occlusive member is subjected to a force or pressure;
   wherein the vaso-occlusive member defines and axis, and comprises a key-way that is disposed continuously along the axis of the vaso-occlusive member.

2. The vaso-occlusive device of claim 1, wherein the key-way has a cross-sectional shape that is substantially rectangular.

3. The vaso-occlusive device of claim 1, wherein the key-way has a cross-sectional shape tat is substantially triangular.

4. The vaso-occlusive device of claim 1, wherein a width of the key-way varies.

5. The vaso-occlusive device of claim 1, wherein a depth of the key-way varies.

6. The vaso-occlusive device of claim 1, wherein the key-way exhibits a pitch.

7. The vaso-occlusive device of claim 6, wherein the pitch of the key-way varies.

8. The vaso-occlusive device of claim 6, wherein the pitch of the key-way is constant.

9. The vaso-occlusive device of claim 1, wherein the key-way is disposed along a portion of the vaso-occlusive member in a helical fashion.

10. The vaso-occlusive device of claim 1, wherein pitch of the key-way is relatively tight along a portion of the vaso-occlusive member.

11. The vaso-occlusive device of claim 1, further comprising another key-way disposed continuously along a portion of the vaso-occlusive member.

12. The vaso-occlusive device of claim 11, wherein the key-way and the other key-way are axially spaced from each other.

13. The vaso-occlusive device of claim 11, wherein the key-way and the other key-way intersect.

14. The vaso-occlusive device of claim 1, wherein the key-way is disposed discretely along the vaso-occlusive member.

15. The vaso-occlusive device of claim 14, wherein the key-way is partially disposed about a portion of the circumference of the vaso-occlusive member.

16. The vaso-occlusive device of claim 14, wherein the key-way is completely disposed about the circumference of the vaso-occlusive member.

17. The vaso-occlusive device of claim 14, further comprising another key-way disposed discretely along the vaso-occlusive member.

18. The vaso-occlusive device of claim 17, wherein the key-way and the another key-way are closely spaced.

19. The vaso-occlusive device of claim 1, wherein the vaso-occlusive member is made of a biodegradable material.

20. The vaso-occlusive device of claim 1, wherein the vaso-occlusive member comprises a metal selected from the group consisting of platinum, palladium, rhodium, gold, tungsten, and their alloys.

21. The vaso-occlusive device of claim 20, wherein the vaso-occlusive member comprises an alloy of platinum and tungsten.

22. The vaso-occlusive device of claim 1, wherein the vaso-occlusive member comprises an alloy selected from stainless steels and super-elastic alloys.

23. The vaso-occlusive device of claim 22, wherein the vaso-occlusive member comprises nitinol.

24. The vaso-occlusive device of claim 1, wherein the vaso-occlusive member is substantially rectilinear when in a relaxed configuration.

25. The vaso-occlusive device of claim 1, wherein the vaso-occlusive member is substantially curvilinear when in a relaxed configuration.

26. The vaso-occlusive device of claim 1, wherein the vaso-occlusive member has a secondary relaxed configuration.

27. The vaso-occlusive device of claim 26, wherein the vaso-occlusive member is a helically wounded coil in the secondary relaxed configuration.

28. The vaso-occlusive device of claim 26, wherein the vaso-occlusive member has a tertiary relaxed configuration.

29. The vaso-occlusive device of claim 1, wherein the vaso-occlusive member is coupled to a deployment mechanism.

30. The vaso-occlusive device of claim 29, wherein the deployment mechanism comprises an electrolytically severable junction adapted to detach from a core wire by imposition of an electric current on the core wire.

31. The vaso-occlusive device of claim 1, wherein the vaso-occlusive member is sized to fit within an aneurysm.

32. The vaso-occlusive device of claim 1, wherein a discrete portion of the vaso-occlusive member is made of a relatively flexible material for allowing the vaso-occlusive member to bend at the discrete portion.

33. A catheter assembly for occluding a body cavity, comprising:

a delivery catheter having a distal end; and a vaso-occlusive device detachably coupled to the distal end of the catheter, the vaso-occlusive device defines and axis, and comprising an elongate vaso-occlusive member, the vaso-occlusive member having a fold line, wherein the vaso-occlusive member comprises a key-way for forming the fold line, and the key-way is disposed continuously along the axis of the vaso-occlusive member.

34. The catheter assembly of claim 33, wherein the key-way has a cross-sectional shape that is substantially rectangular.

35. The catheter assembly of claim 33, wherein the key-way has a cross-sectional shape that is substantially triangular.

36. The catheter assembly of claim 33, wherein a width of the key-way varies.

37. The catheter assembly of claim 33 wherein a depth of the key-way varies.

38. The catheter assembly of claim 33 wherein the key-way exhibits a pitch.

39. The catheter assembly of claim 38, wherein the pitch of the key-way varies.

40. The catheter assembly of claim 38, wherein the pitch of the key-way is constant.

41. The catheter assembly of claim 33, wherein the key-way is disposed along a portion of the vaso-occlusive member in a helical fashion.

42. The catheter assembly of claim 33, wherein pitch of the key-way is relatively tight along a portion of the vaso-occlusive member.

43. The catheter assembly of claim 33, wherein the vaso-occlusive device further comprises another key-way disposed continuously along a portion of the vaso-occlusive member.

44. The catheter assembly of claim 43, wherein the key-way and the other key-way are axially spaced from each other.

45. The catheter assembly of claim 43, wherein the key-way and the other key-way intersect.

46. The catheter assembly of claim 33, wherein the key-way is disposed discretely along the vaso-occlusive member.

47. The catheter assembly of claim 46, wherein the key-way is partially disposed about a portion of the circumference of the vaso-occlusive member.

48. The catheter assembly of claim 46, wherein the key-way is completely disposed about the circumference of the vaso-occlusive member.

49. The catheter assembly of claim 46, wherein the vaso-occlusive device further comprises another key-way disposed discretely along the vaso-occlusive member.

50. The catheter assembly of claim 49, wherein the key-way and the another key-way are closely spaced.

51. The catheter assembly of claim 49, wherein the vaso-occlusive member is made of a biodegradable material.

52. The catheter assembly of claim 33, wherein the vaso-occlusive member comprises a metal selected from the group consisting of platinum, palladium, rhodium, gold, tungsten, and their alloys.

53. The catheter assembly of claim 52, wherein the vaso-occlusive member comprises an alloy of platinum and tungsten.

54. The catheter assembly of claim 33, wherein the vaso-occlusive member comprises an alloy selected from stainless steels and super-elastic alloys.

55. The catheter assembly of claim 54, wherein the vaso-occlusive member comprises nitinol.

56. The catheter assembly of claim 33, wherein the vaso-occlusive member is substantially rectilinear when in a relaxed configuration.

57. The catheter assembly of claim 33, wherein the vaso-occlusive member is substantially curvilinear when in a relaxed configuration.

58. The catheter assembly of claim 33, wherein the vaso-occlusive member has a secondary relaxed configuration.

59. The catheter assembly of claim 58, wherein the vaso-occlusive member is a helically wounded coil in the secondary relaxed configuration.

60. The catheter assembly of claim 58, wherein the vaso-occlusive member has a tertiary relaxed configuration.

61. The catheter assembly of claim 33, further comprising a deployment mechanism coupled to a proximal end of the vaso-occlusive member.

62. The catheter assembly of claim 61, wherein the deployment mechanism comprises an electrolytically severable junction adapted to detach from a core wire by imposition of an electric current on the core wire.

63. The catheter assembly of claim 33, wherein the vaso-occlusive member is sized to fit within an aneurysm.

64. The catheter assembly of claim 33, wherein a portion of the vaso-occlusive member is made of a relatively weaker material for forming the fold line.

* * * * *

UNITED STATES PATENT AND TRADEMARK OFFICE
CERTIFICATE OF CORRECTION

PATENT NO. : 7,060,083 B2
APPLICATION NO. : 10/152441
DATED : June 13, 2006
INVENTOR(S) : Brent Gerberding It is certified that error appears in the above-identified patent and that said Letters Patent is hereby corrected as shown below:

On Column 15, line 42
replace "and" before "axis"
with --an--

On Column 17, line 6
replace "and" before "axis"
with --an--

Signed and Sealed this

Twenty-fourth Day of June, 2008

JON W. DUDAS
*Director of the United States Patent and Trademark Office*